United States Patent
McAlister et al.

(10) Patent No.: US 6,716,222 B2
(45) Date of Patent: Apr. 6, 2004

(54) STAPLING AND CUTTING IN RESECTIONING FOR FULL THICKNESS RESECTION DEVICES

(75) Inventors: Gary McAlister, Natick, MA (US); Robert L. Sakal, Bolton, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 191 days.

(21) Appl. No.: 10/083,097

(22) Filed: Feb. 26, 2002

(65) Prior Publication Data

US 2002/0082616 A1 Jun. 27, 2002

Related U.S. Application Data

(63) Continuation of application No. 09/727,051, filed on Nov. 30, 2000.

(51) Int. Cl.⁷ .................................. A61B 17/04
(52) U.S. Cl. .................. 606/139; 227/179.1; 227/180.1
(58) Field of Search .............. 606/139; 227/179.1, 227/180.1

(56) References Cited

U.S. PATENT DOCUMENTS

| | | | | |
|---|---|---|---|---|
| 3,552,626 A | * | 1/1971 | Astafiev et al. ............... 227/76 |
| 3,638,652 A | * | 2/1972 | Kelley ...................... 227/179.1 |
| 4,485,817 A | * | 12/1984 | Swiggett ................... 227/179.1 |
| 4,589,582 A | * | 5/1986 | Bilotti .......................... 227/19 |
| 5,037,021 A | * | 8/1991 | Mills et al. ............... 227/175.1 |
| 5,047,027 A | * | 9/1991 | Rydell ......................... 606/48 |
| 5,197,649 A | * | 3/1993 | Bessler et al. ........... 227/179.1 |
| 5,395,030 A | * | 3/1995 | Kuramoto et al. ........ 227/179.1 |
| 5,445,644 A | * | 8/1995 | Pietrafitta et al. ........... 606/151 |
| 5,458,112 A | * | 10/1995 | Weaver ...................... 600/566 |
| 5,569,277 A | * | 10/1996 | Evans et al. ................ 606/159 |
| 5,603,250 A | * | 2/1997 | Robinson ....................... 82/56 |
| 5,609,285 A | * | 3/1997 | Grant et al. ............. 227/179.1 |
| 5,643,304 A | * | 7/1997 | Schechter et al. .......... 606/171 |
| 5,868,760 A | * | 2/1999 | McGuckin, Jr. ............ 606/139 |
| 5,928,163 A | * | 7/1999 | Roberts et al. ............. 600/567 |
| 5,947,983 A | * | 9/1999 | Solar et al. ................. 606/144 |

* cited by examiner

*Primary Examiner*—Gary Jackson
(74) *Attorney, Agent, or Firm*—Fay Kaplun & Marcin, LLP

(57) ABSTRACT

A stapling unit for use with an endoscopic stapling system adapted to be advanced along an endoscope to a predetermined location within a body lumen to staple the portion of tissue, as part of an occlusal or full thickness resectioning procedure. The stapling unit comprises a first casing having a distal end, a proximal end and a stapling device mounted thereto adjacent to a first window extending through a periphery of the first casing. The invention includes methods for the stapling, severing and removal of tissue by using the device.

16 Claims, 14 Drawing Sheets

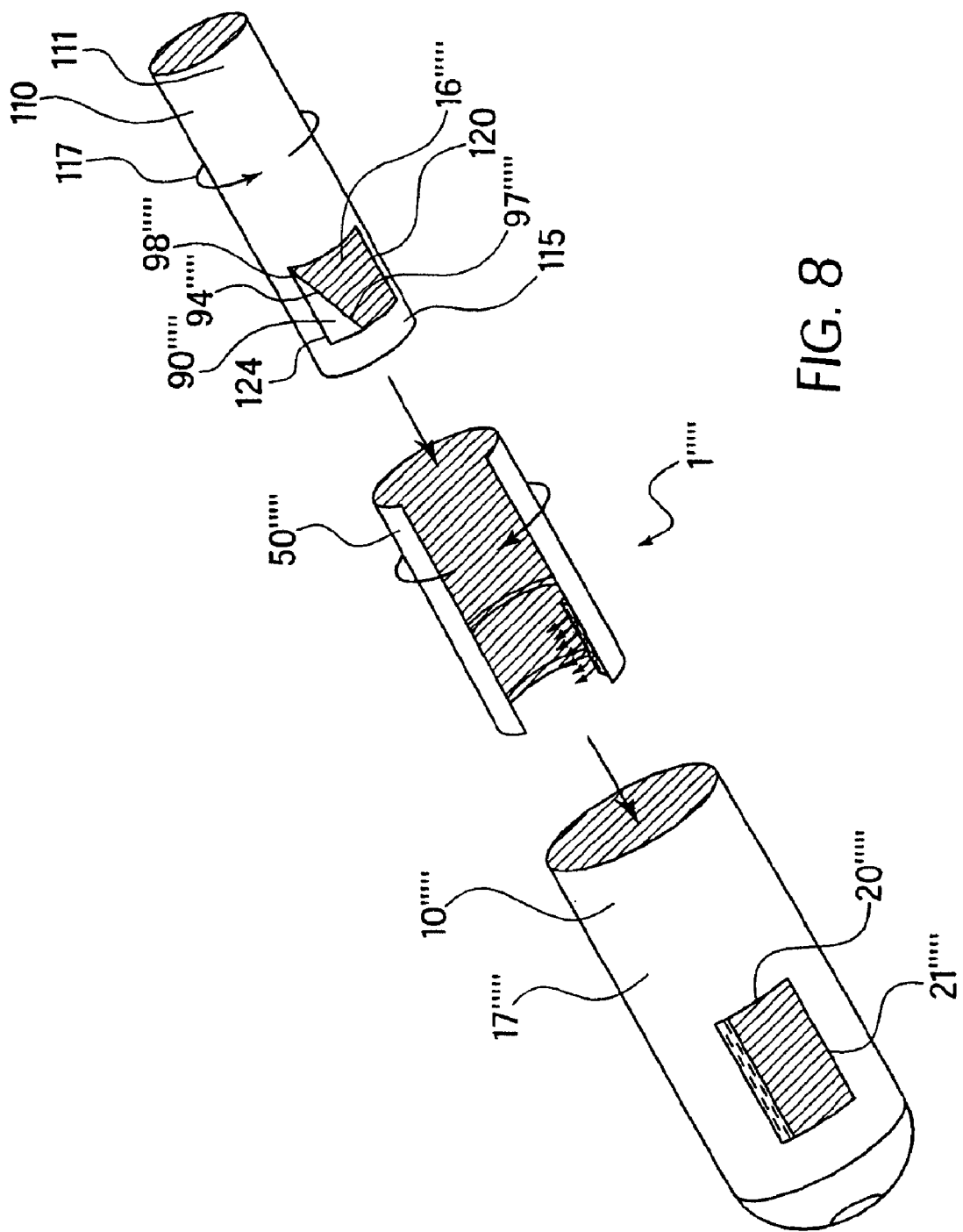

STAPLING AND CUTTING IN RESECTIONING FOR FULL THICKNESS RESECTION DEVICES

The present application is a continuation of application Ser. No. 09/727,051, filed Nov. 30, 2000, entitled "Stapling and Cutting in Resectioning for Full Thickness Resection Devices".

FIELD OF THE INVENTION

The present invention relates to a device and method for stapling tissue, and more specifically, to grasping, stapling, and cutting tissue within a body lumen.

BACKGROUND INFORMATION

When tissue surrounding a body lumen becomes cancerous or otherwise diseased, it is often necessary to remove the diseased tissue for analysis or disposal. Conventional devices and methods for such tissue removal often require open surgery to access the diseased tissue.

In addition, endoluminal tissue cutters have been known, e.g., U.S. Pat. No. 5,947,983, issued to Solar et al. ("the Solar patent"), the entire disclosure of which is expressly incorporated herein by reference. Many of these devices relied on sutures to close the resulting wound. However, these devices have often been unwieldy as the manipulation of sutures from outside the body can be extremely difficult.

SUMMARY OF THE INVENTION

The present invention is directed to a stapling unit for use with an endoscopic stapling system comprising a first casing adapted to be advanced along an endoscope to a predetermined location within a body lumen, the first casing having a distal end, a proximal end and a stapling device mounted thereto adjacent to a first window extending through a periphery of the first casing.

BRIEF DESCRIPTION OF THE DRAWINGS

FIG. 1A illustrates a first view of a first embodiment of a device according to the present invention.

FIG. 1B illustrates a second view of the first embodiment of FIG. 1A.

FIG. 1C illustrates a third view of the first embodiment of FIG. 1A.

FIG. 1D illustrates a fourth view of the first embodiment of FIG. 1A.

FIG. 3A illustrates the stapling device according to the present invention in a stapler retracted position.

FIG. 3B illustrates the stapling device of FIG. 3A in a stapler engaged position.

FIG. 3C illustrates the stapling device of FIGS. 3A and 3B in a stapler engaged position.

FIG. 5A illustrates a first view of the fourth embodiment of a device according to the present invention.

FIG. 5B illustrates a second view of the fourth embodiment of FIG. 5A.

FIG. 7A illustrates the tissue cutter of FIG. 5A in a cutter retracted position.

FIG. 7B illustrates the tissue cutter of FIG. 5A in a cutter engaged position.

FIG. 7C illustrates the tissue cutter of FIGS. 5A in a cutter complete position.

FIG. 8 illustrates a sixth embodiment of a device according to the present invention.

DETAILED DESCRIPTION OF THE INVENTION

The present invention provides for the stapling and removal of tissue within a body lumen without resorting to open surgery and allows for the identification of tissue desired for stapling and removal from a body lumen. The device makes possible accurate, localized in-situ stapling of tissue and the severing of tissue below the staple line. A full thickness portion of a body lumen wall can be extracted quickly and simply minimizing and/or eliminating bleeding or leakage from the lumen.

Figure 1A:
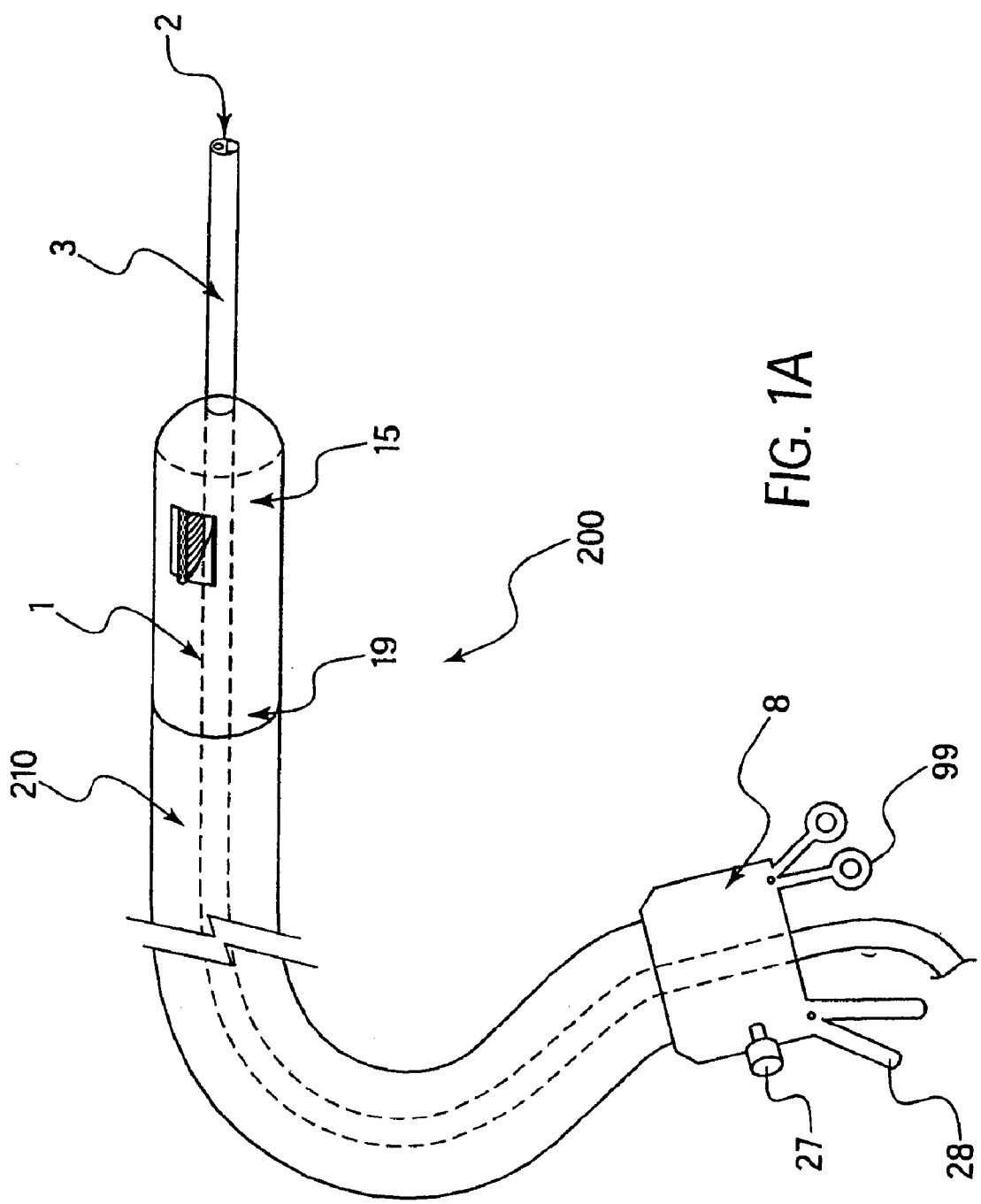
FIGS. 1A–1D illustrate a first embodiment of a device according to the present invention.
Figure 1B:
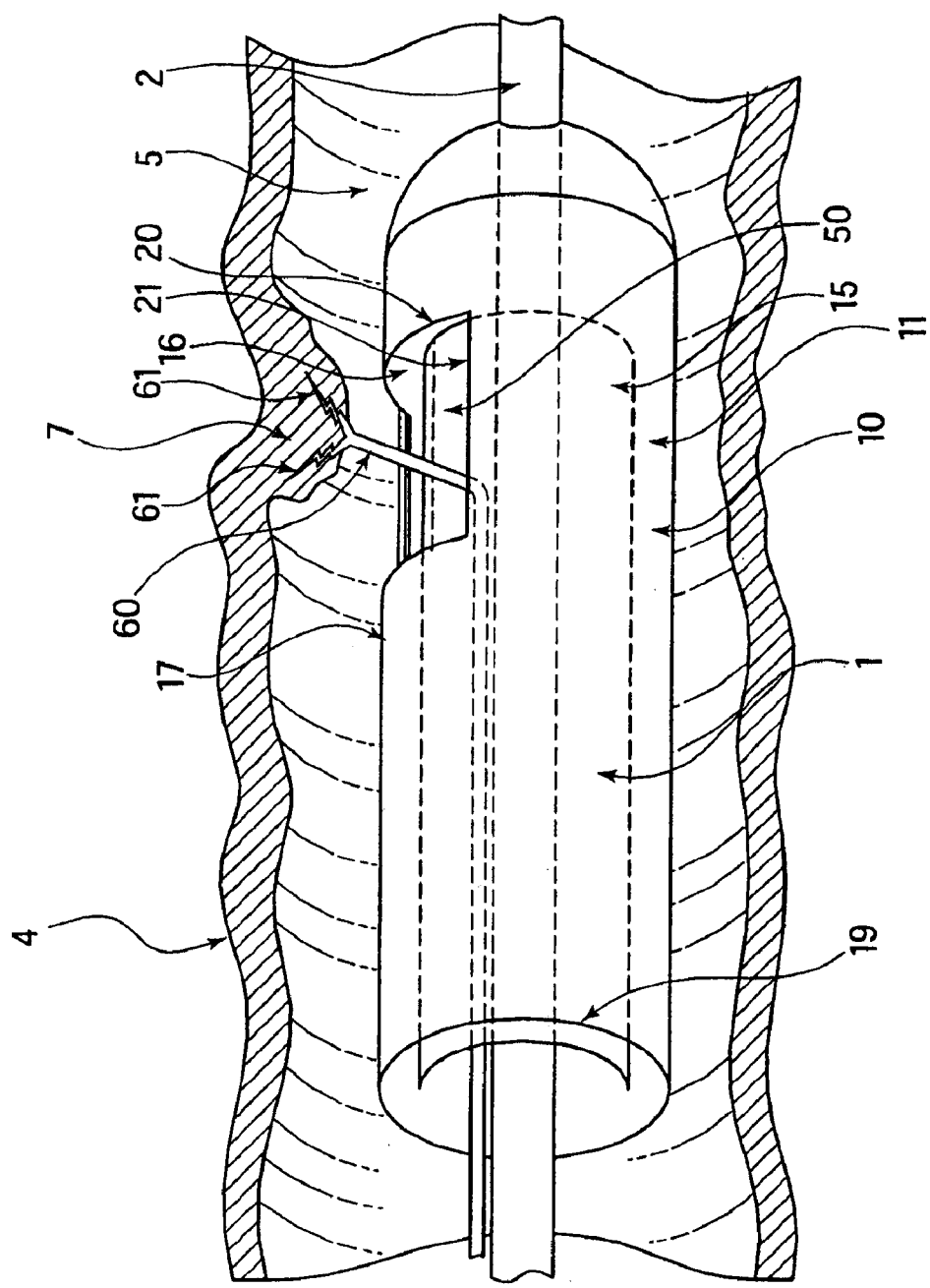

FIGS. 1A–1D show a device according to the present invention. As shown in FIGS. 1A and 1B, the stapling unit 1 is part of an endoscopic stapling system 200, which comprises an endoscope 3, a control unit 8, and a shaft 210. The endoscope 3 for use with the current invention may preferably be a gastroscope or end-viewing endoscope 2 for real-time viewing of an interior 5 of a body lumen 4. The stapling unit 1 may be positioned adjacent to a portion of tissue to be stapled 7 by first insufflating the body lumen 4 and locating the portion of tissue visibly using the endoscope 3. The stapling unit may then be advanced distally along the endoscope 3 to a desired position relative to the portion of tissue 7. The stapling unit 1 can be operated remotely via a control unit 8 located outside the body during use.

Figure 1C:
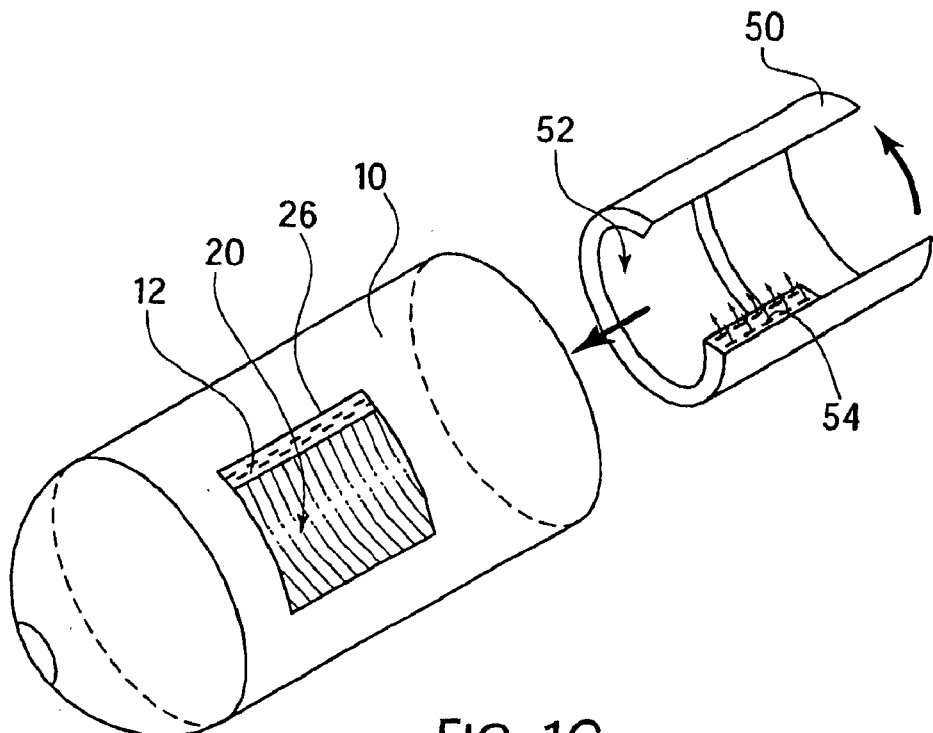
Figure 1D:
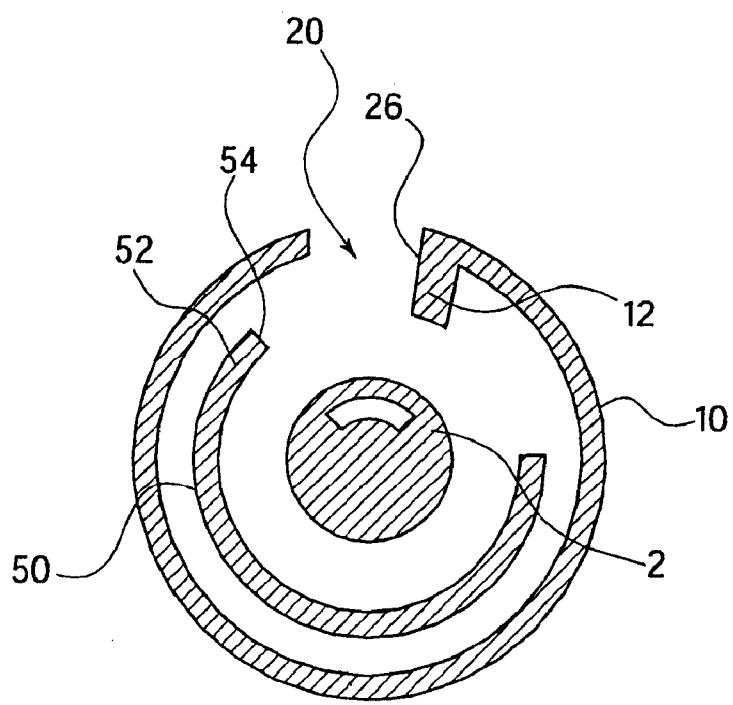

FIG. 1B details the stapling unit 1 in one embodiment which can be used, for example, in an occlusal procedure. The stapling unit 1 comprises a first casing 10, which may, for example, be formed as a partially tubular member 11. The stapling unit 1 has a window 20 formed in a distal portion 15 thereof exposing an interior 16 of the stapling unit 1 to an exterior 17 of the stapling unit 1. A stapling device 50 is mounted to the unit 1 adjacent to the window 20. If an end-viewing endoscope 2 is used to find the location of the portion of tissue to be stapled 7 and kept at the location after the stapling unit 1 has been positioned there, an operator can continuously view the work done on the portion of tissue 7 by looking through the window 20 from an interior of the stapling unit 1 to an interior 5 of the body lumen 4. FIGS. 1C and 1D detail each component of the stapling unit 1. The window 20 optionally has a fixed perimeter and shape, which may, for example be rectangular. One edge 26 of the window 20 may form an anvil 12. The stapling device 50 may have a movable staple head 52, forming a staple firing edge 54, which, when the stapling device 50 is mounted in the first casing 10, faces the anvil 12.

Figure 2A:
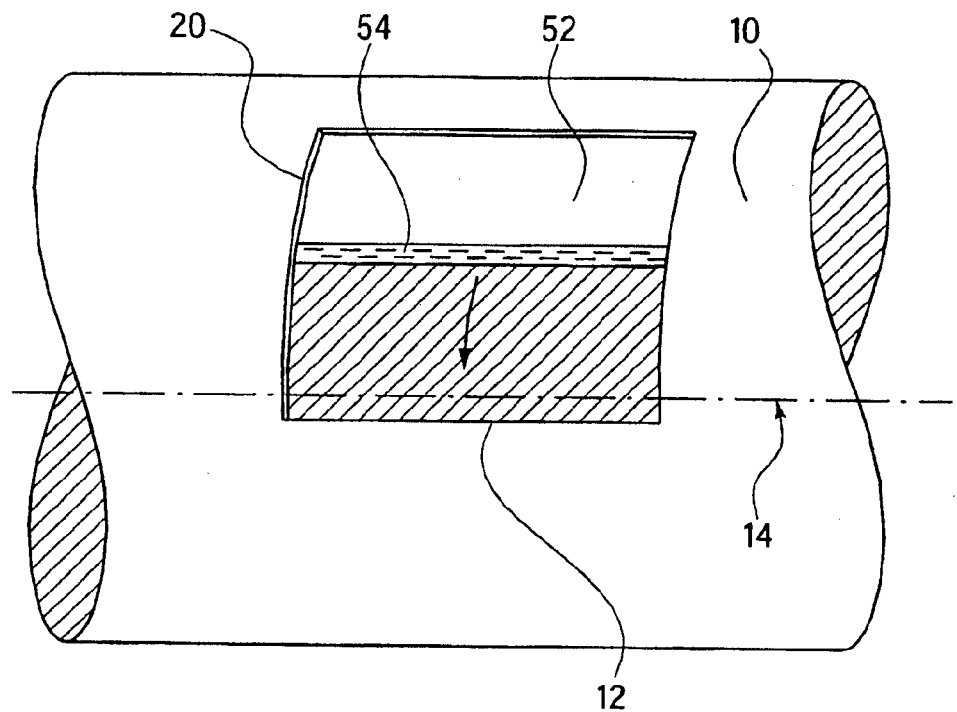
FIG. 2A illustrates a configuration of the first embodiment of FIG. 1A, wherein the components move rotationally with respect to each other.

The orientation and movement of the components in the first embodiment is shown in FIG. 2A. The stapling head 52 may be rotatably mounted within the first casing 10 so that, in a first position, the staple firing edge 54 is adjacent to the anvil 12. The stapling unit 1 may rotate, for example, about an axis substantially parallel to a longitudinal axis 14 of the first casing 10. Then, the staple head 52 is rotated relative to the first casing 10, to a second position.

Figure 2B:
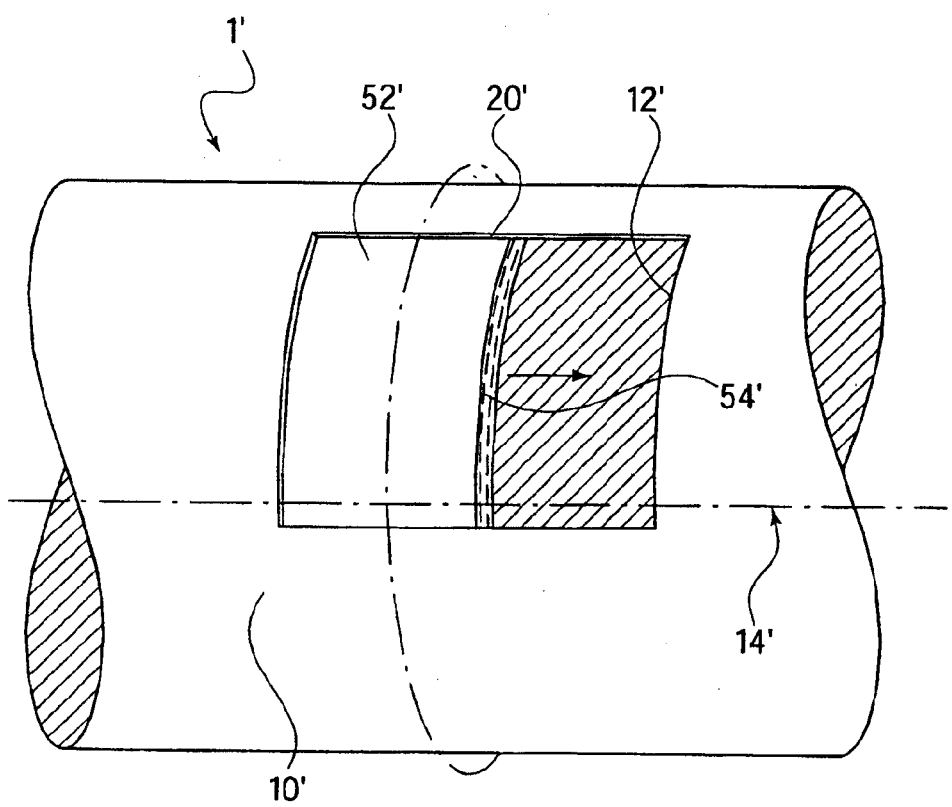
FIG. 2B illustrates a configuration of a second embodiment of the present invention, wherein the components move longitudinally with respect to each other.

An alternative orientation and movement of the components is shown in a second embodiment of a device according to the present invention, shown in FIG. 2B. In the second embodiment, the stapling head 52' may be movably mounted in a longitudinal direction within the first casing 10' so that, in a first position, the staple firing edge 54' is adjacent to the anvil 12'. The stapling unit 1' may move longitudinally, for example, parallel to an axis substantially parallel to a longitudinal axis 14' of the first casing 10'. Then, the stapling head 52' is moved longitudinally relative to the first casing 10', to a second position.

Figure 3A:
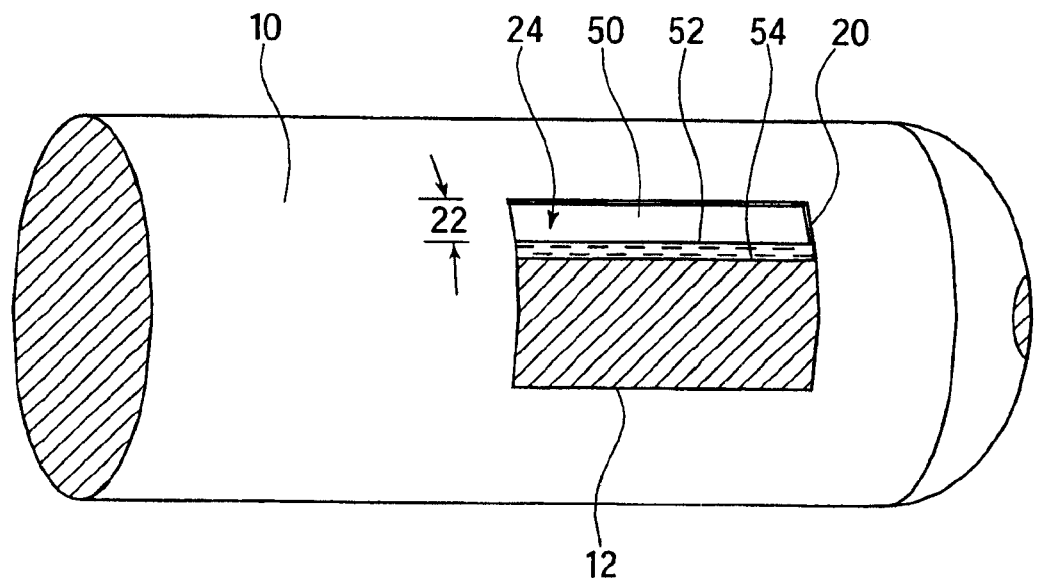
FIGS. 3A–3C illustrate movement of a stapling device according to the present invention from a stapler retracted position to a stapler engaged position.
Figure 3B:
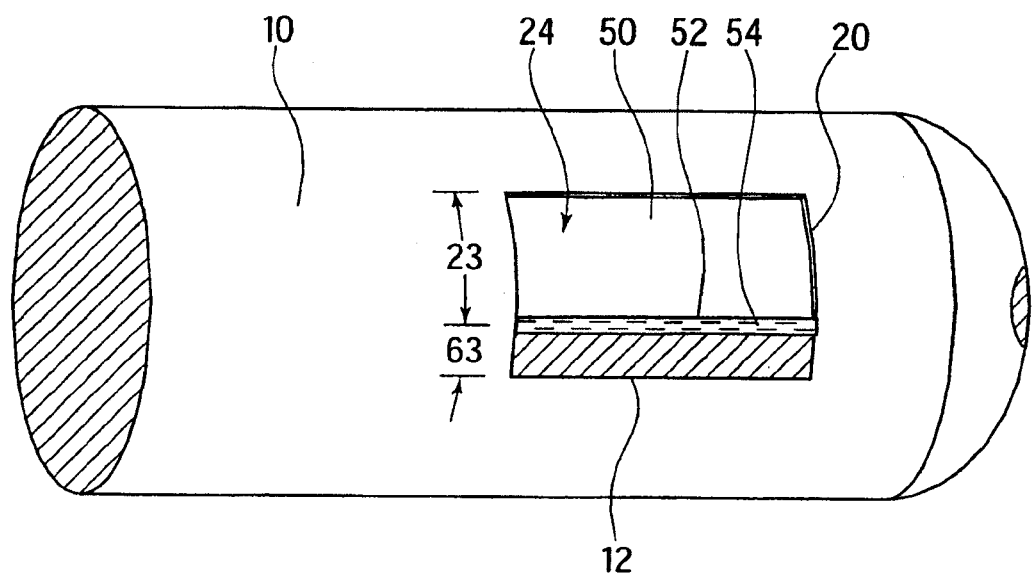
Figure 3C:
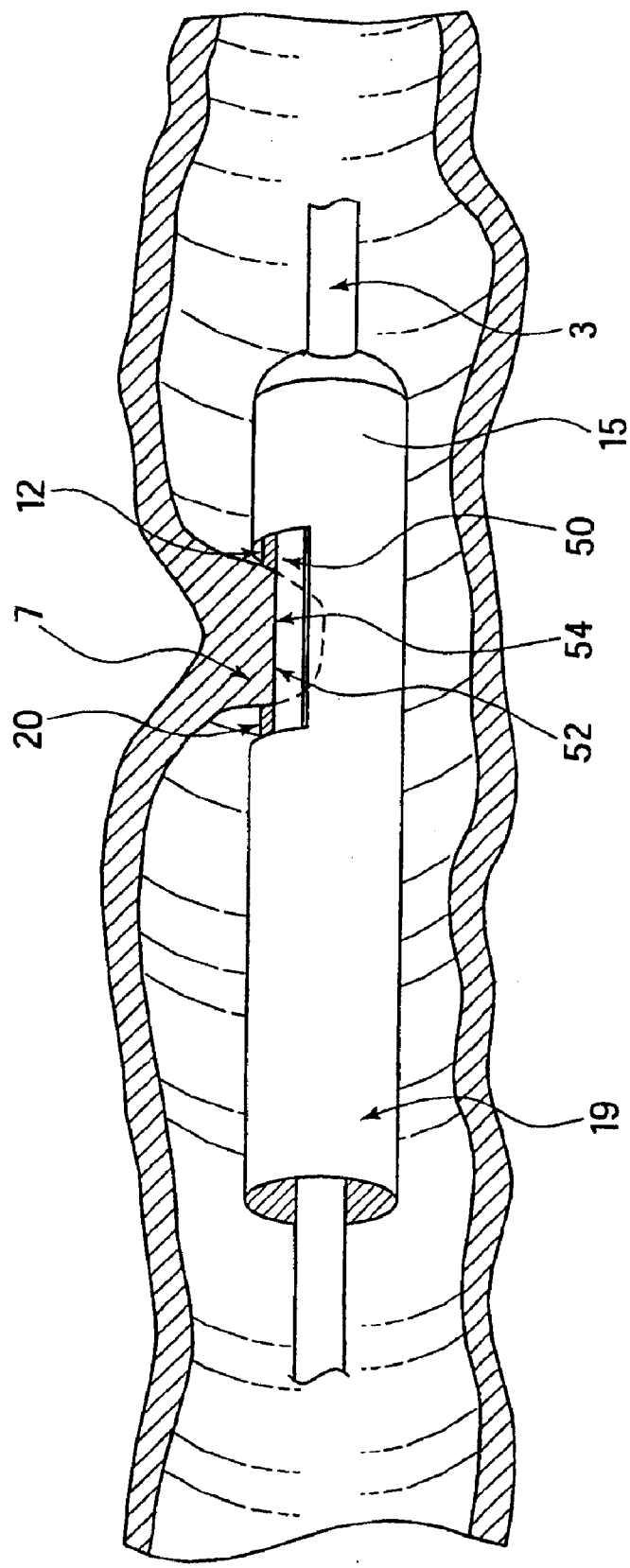

Returning to the orientation and movement of the components in the first embodiment of the device according to the present invention, as detailed in FIGS. 3A–3C, the stapling device 50 can be mounted so that the staple head 52 covers a portion 24 of the window 20, while being movably coupled to the first casing 10. The size of the portion 24 of window 20 covered varies depending on whether the staple head 52 has been moved relative to the first casing 10 between a stapler retracted position (detailed in FIG. 3A) and a stapler engaged position (detailed in FIGS. 3B and 3C). When the staple head 52 is in the stapler retracted position, the staple head 52 covers a smaller portion 22 of window 20 to provide space for drawing the portion of tissue to be stapled 7 into the window 20. When the staple head 52 is moved to the stapling position, the staple head 52 covers a larger portion 23 of the window 20 so that a portion of tissue 7 received in the window 20 is grasped between the staple firing edge 54 and the anvil 12.

As shown in FIG. 3B, the distance between the staple firing edge 54 and the anvil 12 when the staple head 52 is in the stapling position is a predetermined stapling distance or thickness 63. The stapling device 50 may optionally have a position adjusting mechanism 27 (shown in FIG. 1A), operated using the control unit 8, to adjust this predetermined stapling distance 63 before firing staples (not shown) from the staple firing edge 54, through the tissue 7 and against the anvil 12. The stapling unit 1 can have a stapling actuating mechanism 28 (shown in FIG. 1B), also operated using the control unit 8 and coupled between the stapling device 50 and a proximal end 19 of the unit 1 to activate the staple head 52 to fire staples (not shown) from the staple firing edge 54, through the tissue 7, and against the anvil 12 to staple the portion of tissue 7 grasped between the staple firing edge 54 and the anvil 12.

Figure 4:
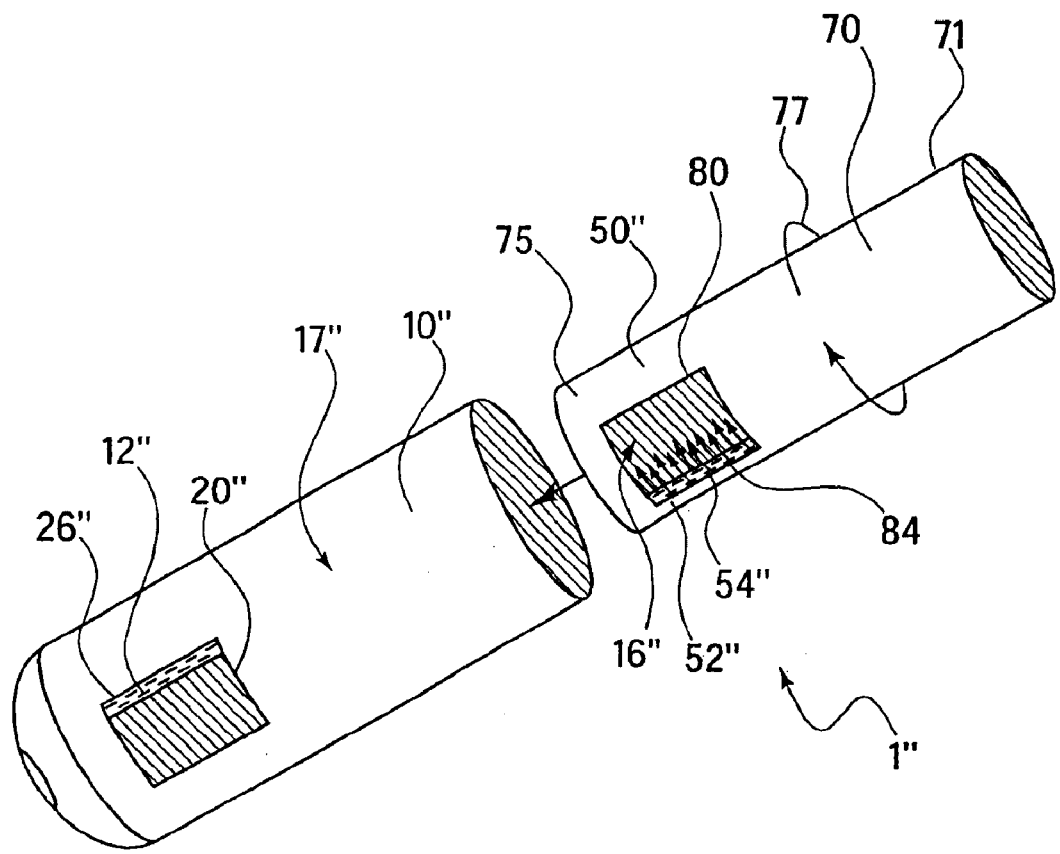
FIG. 4 illustrates a third embodiment of a device according to the present invention.

A third embodiment of a device according to the present invention shown in FIG. 4 is similar to the first embodiment except that in the third embodiment, the stapling device 50" may be mounted onto a second casing 70. The second casing 70, may, for example, be partially tubular member 71, which also has a window 80 formed in a distal portion thereof. The window 80 faces the window 20" of the first casing 10" when the second casing 70 and first casing 10" are in a predetermined alignment with respect to one another to form an opening from an interior 16" of the stapling unit 1" to an exterior 17" of the stapling unit 1". The staple firing edge 54" is positioned on an edge 84 of the window 80 and facing the anvil 12" which is formed on an opposing edge 26" of the window 20" so that moving the staple head 52" from the stapler retracted position to the stapling position translates into moving the distal portion 75 of the second casing 70, changing the predetermined alignment of the windows 20" and 80 so that the staple firing edge 54" is moved towards the anvil 12" in direction 77.

Figure 5A:
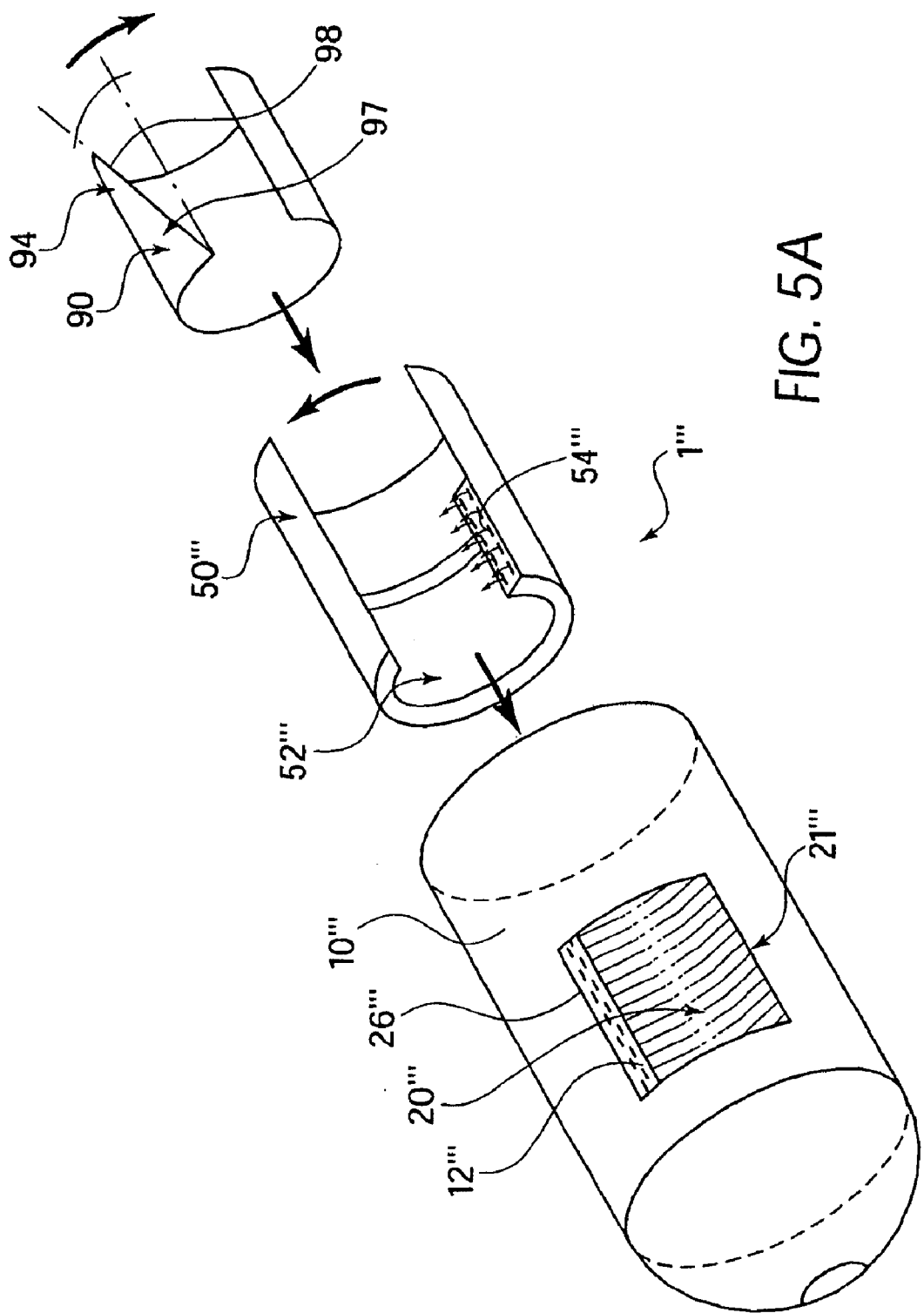
FIGS. 5A–5B illustrates a fourth embodiment of a device according to the present invention.
Figure 5B:
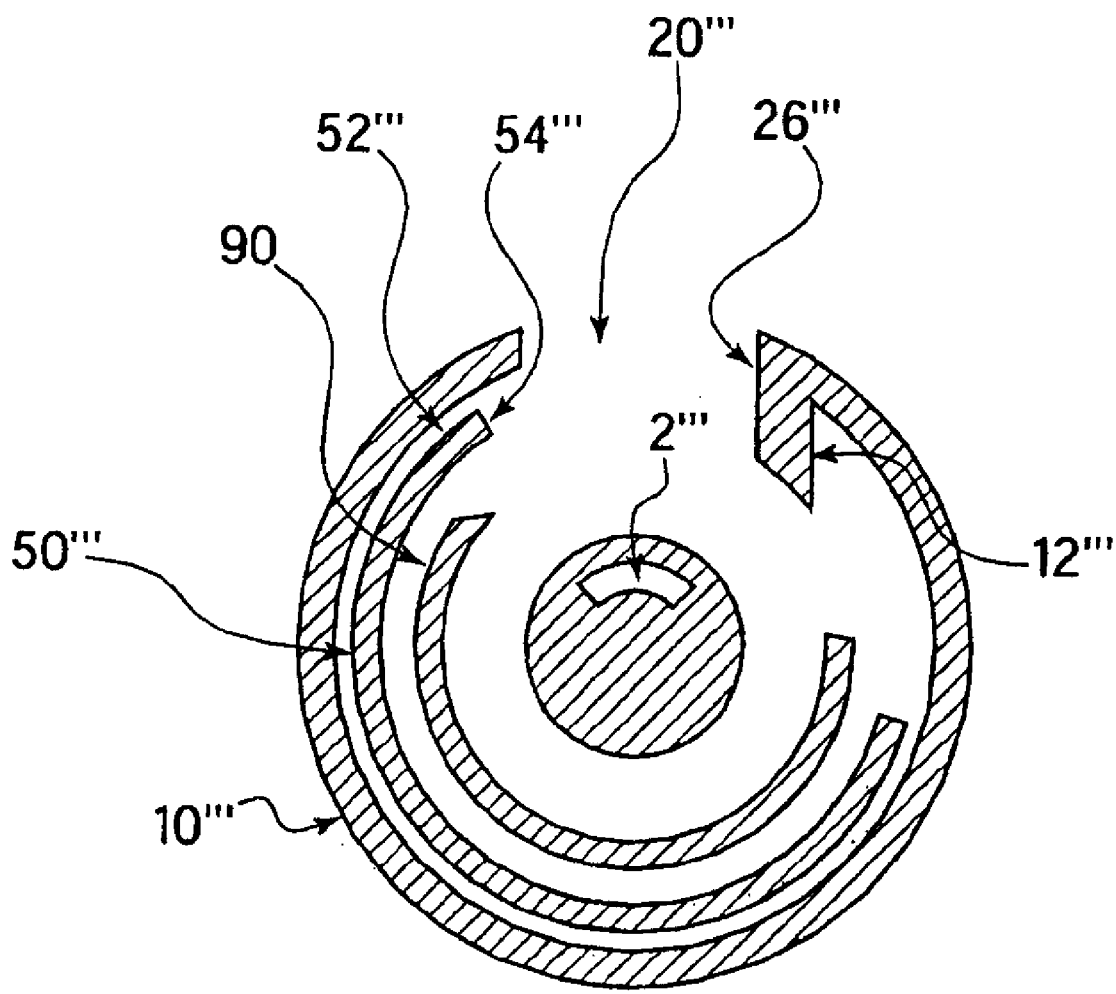

A fourth embodiment of a device according to the present invention shown in FIGS. 5A and 5B is similar to the first embodiment except that in the fourth embodiment, the stapling unit 1'" may also have a tissue cutter 90. The tissue cutter 90 enables the stapling unit 1'" to be used, for example, for full thickness resectioning procedures during which a portion of tissue below the staple line is severed and removed from the body lumen 4 for testing.

Figure 6A:
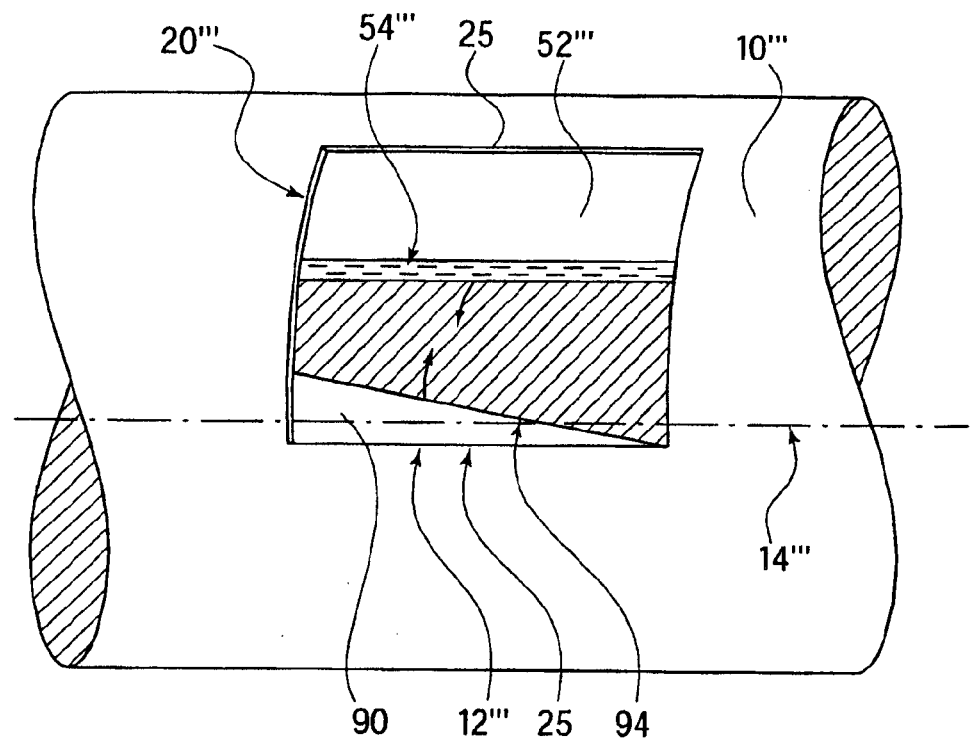
FIG. 6A illustrates a configuration of the fourth embodiment of FIG. 5A, wherein the components move rotationally with respect to each other.

The orientation and movement of the components in the fourth embodiment is shown in FIG. 6A. The cutting edge 94 may be rotatably mounted within the first casing 10'" so that, in a first position, the cutting edge 94 is adjacent to a side 25 of the window 20'" which is substantially parallel to a longitudinal axis 14'" of the first casing 10'". The tissue cutter 90 may rotate, for example, about an axis substantially parallel to a longitudinal axis 14'" of the first casing 10'". Then, the cutting edge 94 is rotated relative to the first casing 10'" to cut the issue grasped between the staple device 50'" and the anvil 12'".

Figure 6B:
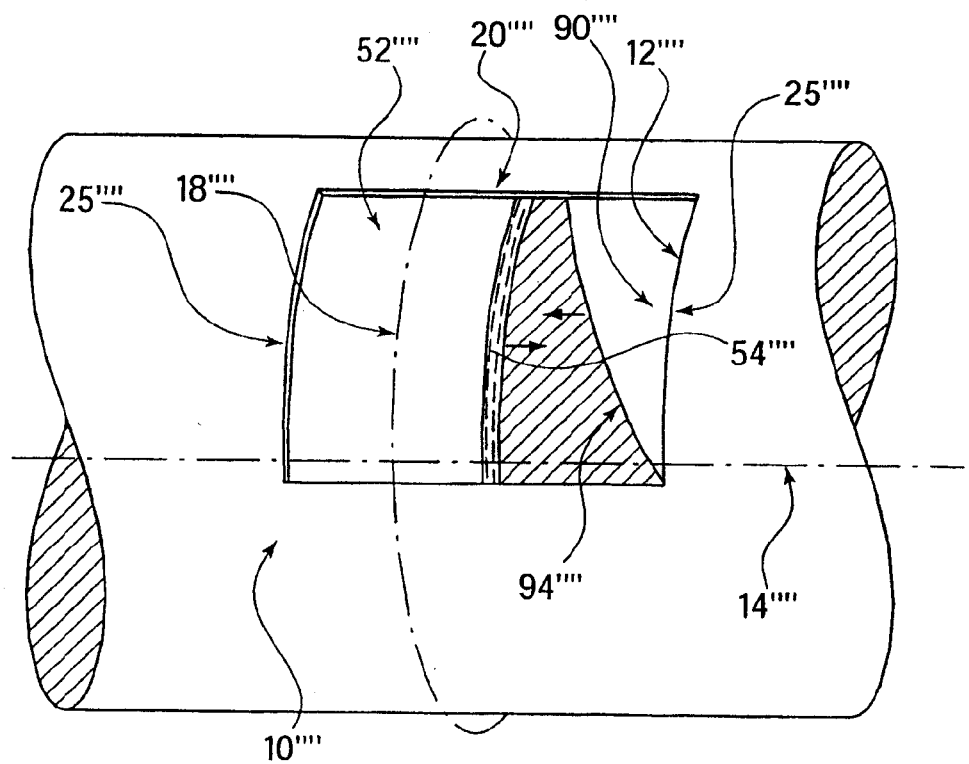
FIG. 6B illustrates a configuration of a fifth embodiment of the present invention, wherein the components move longitudinally with respect to each other.

An alternative orientation and movement of the components is shown in a fifth embodiment of a device according to the present invention, shown in FIG. 6B. In the fifth embodiment, the tissue cutter 90"" is movably mounted in a longitudinal direction within the first casing 10"" so that, in a first position, the cutting edge 94"" is adjacent to a side 25"" of the window 20"" which is substantially parallel to a circumference 18"" of the first casing 10"". When the tissue cutter 90"" is moved axially relative to the first casing 10"" and stapling device 50"" along the longitudinal axis 14"" of the first casing 10"" the cutting edge 94"" severs the tissue grasped by the staple device and the anvil.

Figure 7A:
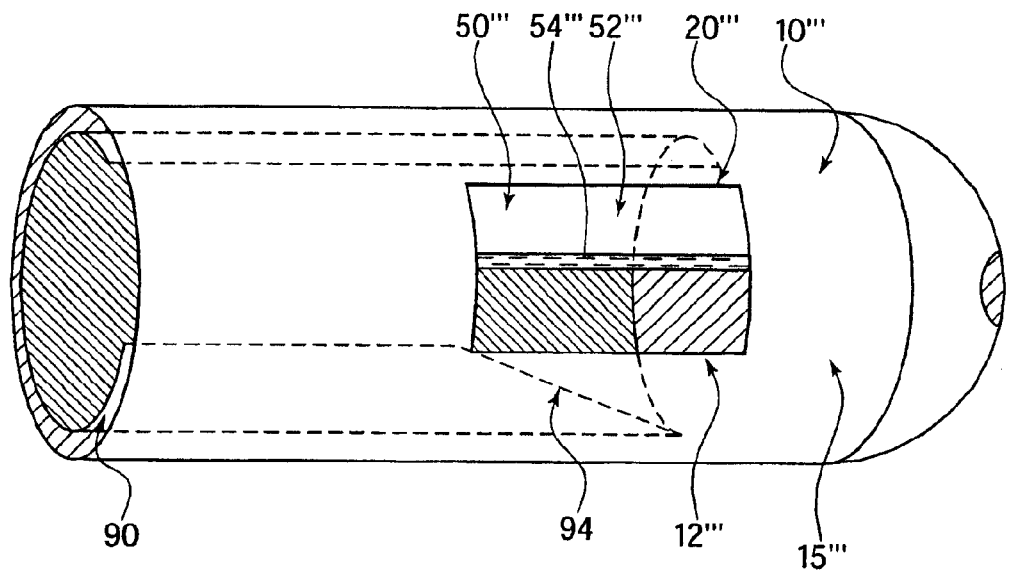
FIGS. 7A–7C illustrate movement of the tissue cutter in the fourth embodiment of FIG. 5A according to the present invention from a cutter engaged position to a cutter complete position.
Figure 7B:
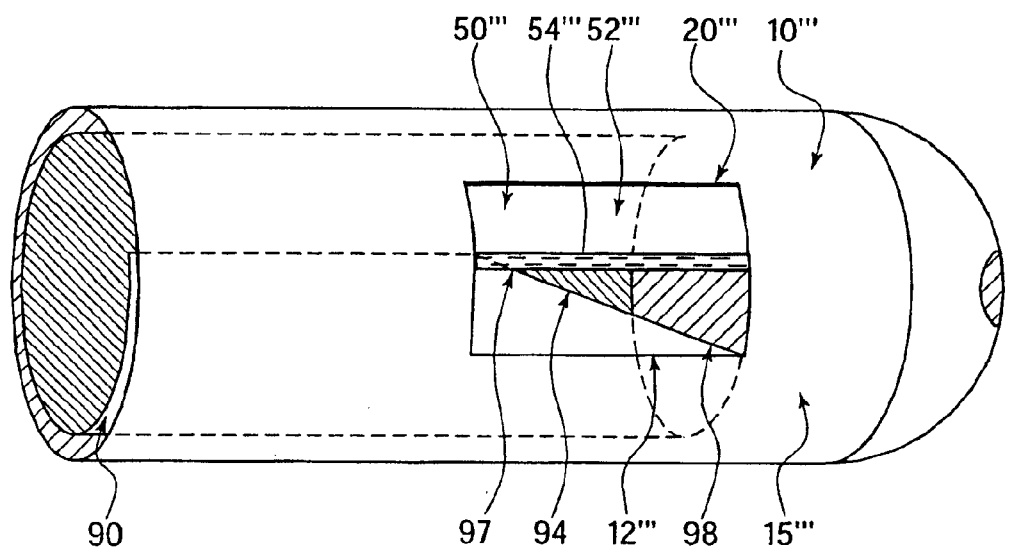
Figure 7C:
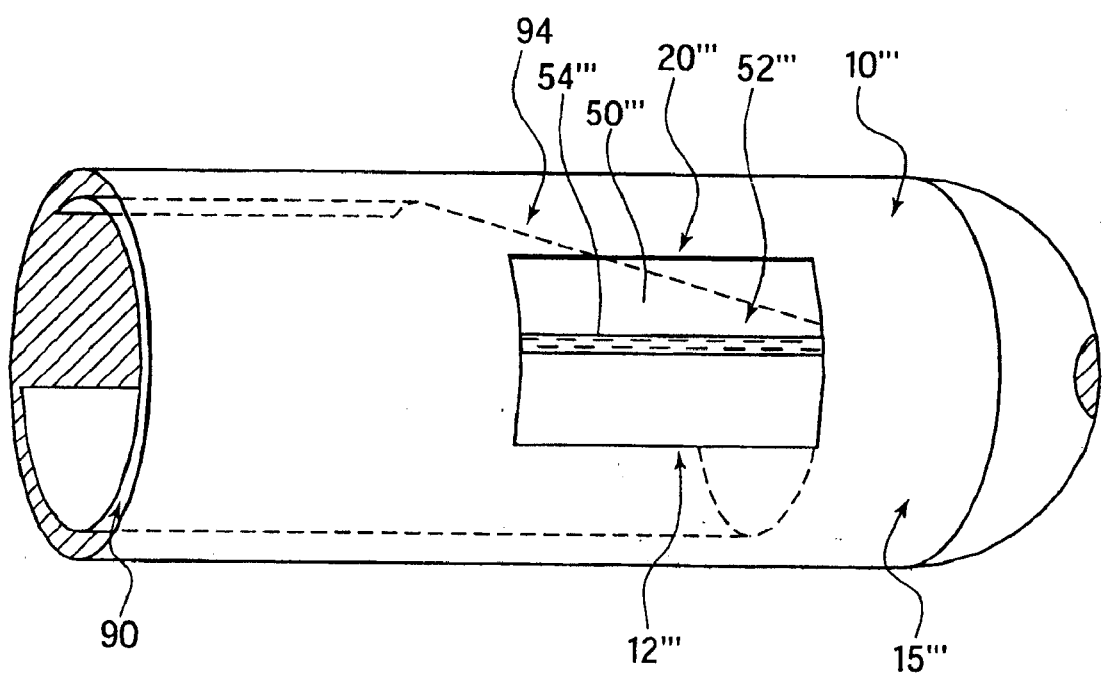

Returning to the orientation and movement of the components in the fourth embodiment of the device according to the present invention, as detailed in FIGS. 7A–7C, the tissue cutter 90 is movably mounted to the stapling device 50'" and the first casing 10'" adjacent to the window 20'". The tissue cutter 90 is movable between a retracted position (shown in FIG. 7A), where the tissue cutter 90 is withdrawn from the window 20'", and a tissue cutting position (shown in FIG. 7B), where the tissue cutter 90 is engaged with a portion of tissue 9 to be severed. The tissue cutter 90 has a cutting edge 94 which is angled such that a first portion 97 of the cutting edge 94 contacts the portion of tissue 9 to be severed before a second portion 98 of the cutting edge 94, i.e., the cutting edge 94 is preferably formed as an angled blade.

Once a portion of tissue has been severed, the tissue cutter 90 is moved to a cutter complete position (detailed in FIG. 7C), covering the first window 20'" completely and containing the severed portion of tissue within the first casing 10'".

Once contained, the stapling unit 1''' is removed from the body lumen 4''' and opened to retrieve the severed portion of tissue for possible testing. The tissue cutter 90 according to the present invention enables an operator to remove a clean tissue sample from a body lumen.

Movement of the tissue cutter 90 may be controlled by a cutting actuator mechanism 99 (shown in FIG. 1A) coupled between a proximal end 19 of the unit 1 and the tissue cutter 90, and operated remotely via the control unit 8. The tissue cutter 90 also preferably has a safety mechanism which prevents the operator from engaging the tissue cutter 90 until after the operator determines that all the staples have been properly fired.

A sixth embodiment of a device according to the present invention shown in FIG. 8 is similar to the fourth embodiment except that in the sixth embodiment, the tissue cutter 90'''' may be mounted on a third casing 110. The third casing 110 may, for example, be a partially tubular member 111, which also has a window 120 formed in the distal portion 115 thereof. The window 120 faces the window 20'''' of the first casing 10'''' when the third casing 110, the stapling device 50'''' and first casing 10'''' are in a predetermined alignment with respect to one another to form an opening from an interior 16'''' of the stapling unit 1'''' to an exterior 17'''' of the stapling unit 1''''. The cutting edge 94'''' is positioned adjacent to an edge 124 of the window 120, and the cutting edge 94'''' preferably may still be angled as shown in FIGS. 5A and 7B, so that a first portion 97'''' of the cutting edge 94'''' contacts the tissue to be cut before a second portion 98'''' of the cutting edge 94''''. Rotational movement of the tissue cutter 90'''' from the retracted position to the tissue cutting position translates into rotational movement of the distal portion 115 of the third casing 110, changing the predetermined alignment of the windows 20'''' and 120 so that the cutting edge 94'''' is moved towards the opposing edge 21'''' of the window 20'''' on the first casing 10'''' in direction 117.

Figure 9:
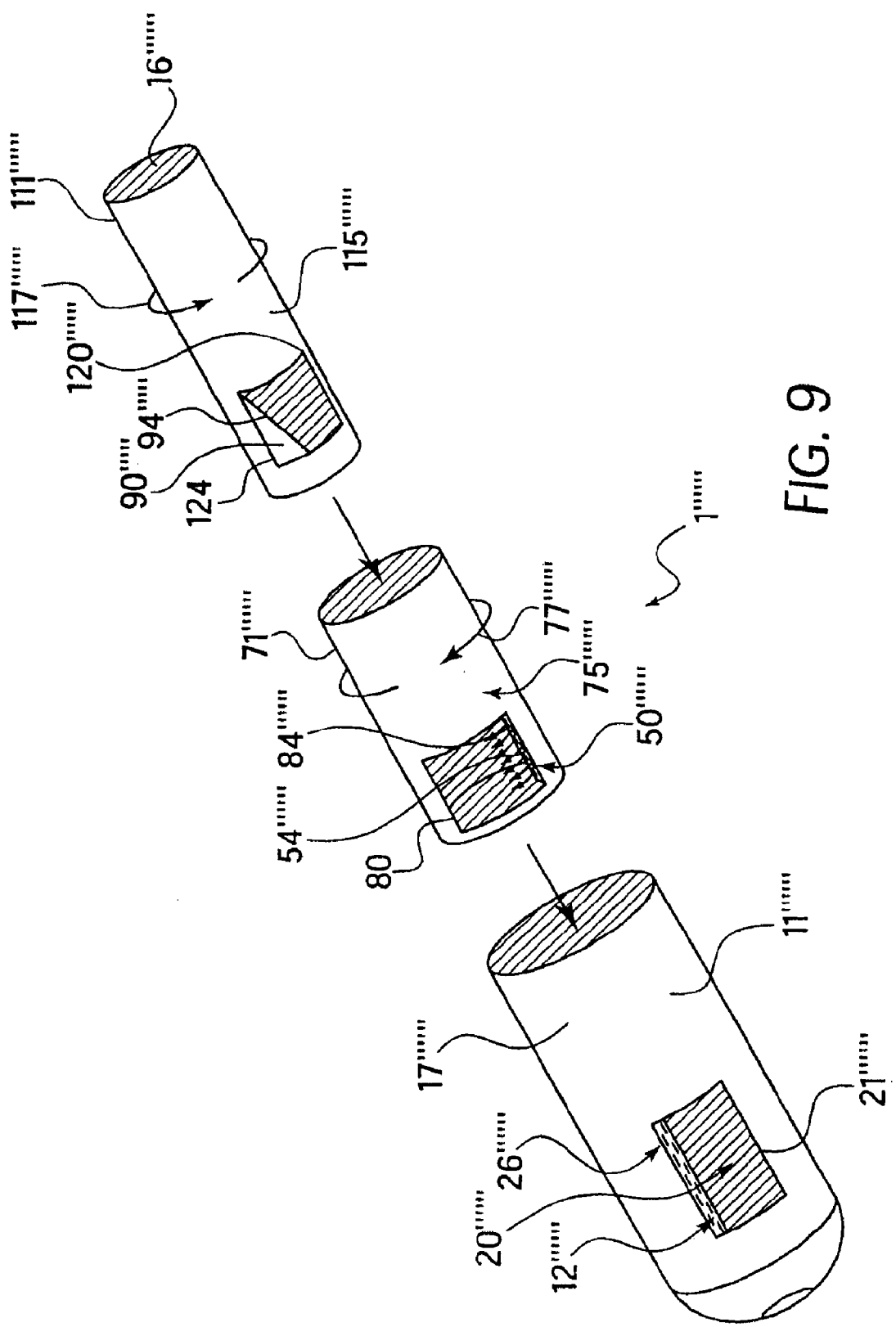
FIG. 9 illustrates a seventh embodiment of a device according to the present invention.

In a seventh embodiment detailed in FIG. 9, the stapling unit 1''''' operates similarly as described above, but is comprised of three concentric tubes 11''''', 71''''' and 111''''' with windows 20''''', 80''''', and 120''''' which form an opening 124''''' from an interior 16''''' of the stapling unit 1''''' to an exterior 17''''' of the stapling unit 1'''''. One edge 26''''' of the window 20''''' on the first tube 11''''' forms an anvil 12'''''. The stapling device 50''''' is mounted to second tube 71''''' which is movably mounted within the first tube 11''''', and an edge 84''''' on the window 80''''' on the second tube 71''''' forms a staple firing edge 54''''' which faces the anvil 120'''''. The tissue cutter 90''''' is mounted to the third tube 111''''' which is movably mounted within the second tube 71''''' and the first tube 11''''', and an edge 124''''' of the window 120''''' on the third tube 111''''' forms the cutting edge 94'''''.

Any of the embodiments of the present invention may optionally includes a tissue grasper 6 (detailed in FIG. 1B) within the stapling unit 1, to draw the portion of tissue 7 to be stapled and the portion of tissue to be cut into the window 20 to an interior 16 of the stapling unit 1 when the stapling device 50 and tissue cutter 90 are withdrawn to retracted positions. As known in the art, the tissue grasper 60 grabs the portion of tissue 7 with, for example, a pair of jaws 61, while a vacuum tube (not shown) sucks tissue 7 through the window 20 by creating negative pressure within the window 20. Alternatively, suction may be applied through the device to draw the portion of tissue 7 to be stapled and the portion of tissue 9 to be cut into the window 20 to an interior 16 of the stapling unit 1.

The present invention provides a device and method for the minimally-invasive grasping, stapling and removal of diseased tissue from within a body lumen. Those with skill in the art may recognize various modifications to the embodiments of the invention described and illustrated herein. Such modifications are meant to be covered by the spirit and scope of the appended claims.

What is claimed is:

1. A system for endolumenally resecting tissue comprising:
    a flexible endoscope;
    an operative housing slidably coupleable to the endoscope and including a fixed perimeter window extending through an exterior wall thereof, an anvil formed on a first edge of the window and a stapling apparatus mounted within the housing for movement between a stapling position in which a staple firing surface of the stapling apparatus is adjacent to the anvil and a tissue receiving position in which the staple firing surface is separated from the anvil to open the window and expose a tissue receiving cavity within an interior of the operative housing; and
    a tissue grasping mechanism for drawing tissue to be resected through the window into the tissue receiving cavity.

2. The system according to claim 1, further comprising:
    a control handle which, when the operative head is in an operative position within a body lumen, remains outside the body; and
    a flexible sheath extending from the control handle to a proximal end of the operative housing, wherein, when in an operative configuration, the endoscope is received within the flexible sheath.

3. The system according to claim 2, wherein the flexible sheath has a column strength sufficient to allow an operator to push the operative housing along the endoscope into a body lumen by pushing the flexible sheath into the body lumen.

4. The system according to claim 1, wherein the operative housing is substantially cylindrical and wherein the stapling apparatus is mounted therein to rotate about an axis of the operative housing between the stapling position and the tissue receiving position.

5. The system according to claim 1, the stapling apparatus is mounted within the operative housing for motion substantially parallel to a longitudinal axis of the operative housing.

6. The system according to claim 1, wherein the operative housing is substantially cylindrical and wherein the stapling apparatus is mounted therein to rotate about an axis of the operative housing between the stapling position and the tissue receiving position.

7. The system according to claim 1, wherein the operative housing includes an endoscope receiving lumen extending therethrough from a proximal opening to a distal opening formed in a distal end of the operative housing.

8. The system according to claim 1, further comprising:
    a tissue cutting mechanism mounted within the operative housing for cutting tissue located radially within a portion of tissue stapled by the stapling apparatus.

9. The system according to claim 8, wherein the operative housing is substantially cylindrical and wherein the tissue cutting mechanism includes a partially cylindrical member rotatably mounted within the operative housing radially within the stapling apparatus and including an angled tissue cutting surface.

10. The system according to claim 1, wherein the operative housing is substantially cylindrical and wherein the stapling apparatus is mounted therein to rotate about an axis of the operative housing across the window.

11. The system according to claim 1, wherein the operative housing is substantially cylindrical and wherein the stapling apparatus is mounted therein to move along an axis of the operative housing across the window.

12. A method of endolumenally resecting tissue within a body lumen, comprising the steps of:
   endoscopically locating a portion of tissue to be resected within a body lumen;
   sliding an operative housing along the endoscope to a desired position adjacent to the portion of tissue to be resected, wherein the operative housing includes a fixed perimeter tissue receiving window extending therethrough, an anvil formed on an edge of the window and a stapling apparatus movably mounted within the operative housing;
   moving the stapling apparatus to a tissue receiving position in which the stapling apparatus is separated from the anvil;
   drawing the portion of tissue to be resected into the housing through the window folded over so that two full thicknesses of tissue of the body lumen are received within the window;
   moving the stapling apparatus into a stapling position in which the portion of tissue to be resected is clamped between the stapling apparatus and the anvil;
   driving staples from the stapling apparatus through the two thicknesses of tissue to couple the two thicknesses of tissue to one another; and
   cutting tissue radially within the stapled tissue from the stapled tissue.

13. The method according to claim 12, wherein the stapling apparatus is rotated within the housing between the tissue receiving and stapling positions.

14. The method according to claim 12, wherein the stapling apparatus is moved longitudinally within the housing between the tissue receiving and stapling positions.

15. The method according to claim 12, wherein the operative housing is coupled to a control handle which remains outside the body by a flexible sheath and wherein the operative housing is slid along the endoscope by pushing the flexible sheath into the body lumen.

16. A device for endolumenally resecting tissue comprising:
   an operative housing slidably coupleable to a flexible endoscope and including a fixed perimeter window extending through an exterior wall thereof, an anvil formed on a first edge of the window and a stapling apparatus mounted within the housing for movement between a stapling position in which a staple firing surface of the stapling apparatus is adjacent to the anvil and a tissue receiving position in which the staple firing surface is separated from the anvil to open the window and expose a tissue receiving cavity within an interior of the operative housing; and
   a tissue grasping mechanism for drawing tissue to be resected through the window into the tissue receiving cavity.

* * * * *